United States Patent [19]

Solomon

[11] 4,277,184
[45] Jul. 7, 1981

[54] DISPOSABLE ORTHOPEDIC IMPLEMENT AND METHOD

[76] Inventor: Alan Solomon, 16 Fox Run Rd., Dover, Mass. 02030

[21] Appl. No.: 66,400

[22] Filed: Aug. 14, 1979

[51] Int. Cl.³ .................... B01F 15/02; B01F 13/06; A61F 5/04
[52] U.S. Cl. ................... 366/150; 128/92 R; 366/139; 366/348
[58] Field of Search .............. 366/139, 53, 150, 154, 366/165, 168, 184, 197, 199, 241, 244, 247, 279, 341, 348, 249, 250, 251, 602; 222/137, 229; 128/92 R, 218 R, 218 P

[56] References Cited

U.S. PATENT DOCUMENTS

| 3,323,682 | 6/1967 | Creighton | 222/137 X |
| 3,390,814 | 7/1968 | Creighton | 222/137 |
| 3,603,564 | 9/1971 | Price | 366/247 |

FOREIGN PATENT DOCUMENTS 2736928  3/1979  Fed. Rep. of Germany .......... 366/150

Primary Examiner—Edward J. McCarthy
Attorney, Agent, or Firm—Morse, Altman, Oates & Dacey

[57] ABSTRACT

A disposable orthopedic implement and method therefor, such as a bone cement mixer and dispenser comprising disposable mixer and dispenser elements that cooperate to permit bone cement to be mixed in a closed system and to be dispensed therefrom at a bone situs with minimal exposure to ambient contaminants.

10 Claims, 5 Drawing Figures

DISPOSABLE ORTHOPEDIC IMPLEMENT AND METHOD

BACKGROUND OF THE INVENTION

1. Field of Invention

The present invention relates to the preparation and application of bone cement of the type that is used in orthopedic surgery to seat and secure a metal or plastic prosthesis into living bone. Typically such bone cement is prepared just prior to use as a mixture of a polymerizate, such as liquid methyl methacrylate monomer, and an activator such as a powdered mixture of polymethyl methacrylate, barium sulphate and benzoyl peroxide; is injected as a viscous fluid into the osteopathic site; and is polymerized in situ and in vivo to provide a solid plastic implantation.

2. The Prior Art

In the past, bone cement of the foregoing type has been mixed in one device, i.e., a mixing vessel from which reaction fumes are evacuated through a suction conduit; and then has been transferred to another entirely separate device, e.g., a syringe for application by the surgeon. This transfer of the mixed cement from the mixing vessel to the application syringe of necessity had to include exposure of the mixed cement to the atmosphere and thus to such dangers as: contamination of infectious substances; delays due to unwieldly manipulations; polymerization problems resulting from undue exposure to air; escape of toxic fumes generated during polymerization; and undesirable potential exposure to blood which causes weakening of cement bonding.

SUMMARY OF THE INVENTION

The principal object of the present invention is to provide a disposable orthopedic implement such as a bone cement mixer and dispenser and a method therefor, that avoids the dangers and inherent disadvantages of prior art devices employing two separate devices, one for mixing and another for dispensing, in two separate stages i.e., the mixing and the dispensing, with the required transfer of the mixture and its necessary exposure. More particularly, it is an object of the present invention to provide a disposable orthopedic implement designed, to mix bone cement in and dispense from the same closed system which comprises a chamber, a member reciprocable within the chamber, a mixing member operatively and axially receivable within the reciprocable member, and a means for rotating the mixing member within the chamber. The means for rotating the mixing member may be a pneumatic drill or an electric drill. Furthermore, the chamber, the reciprocable member and the mixing member are preferably made of a rigid polymer.

It is a further object of the present invention to provide a method for mixing bone cement in and for dispensing from one and the same closed system at a bone situs with minimal exposure to ambient contaminants, which method comprises: providing a cylindrical member having a chamber and a plunger for reciprocation within the member, providing a mixing member designed for axial displacement within the plunger, partially inserting the mixing member into the plunger, introducing measured amounts of a powdered cement component and of a liquid cement component into the chamber, inserting the plunger together with the mixing member partly into the chamber so that the mixing member communicates with the introduced amounts of cement components therein, rotating the mixing member so as to mix the cement components within the chamber, completely withdrawing the mixing member into the plunger, and dispensing the mixture from the chamber by axially displacing the plunger within the cylindrical member. All of the mixing and dispensing elements of the bone cement mixer and dispenser of the invention are sterilizable and disposable.

Other objects of the present invention will in part be obvious and will in part appear hereinafter.

The invention accordingly comprises the products and processes of the present disclosure, together with their parts, steps and interrelationships, the scope of which will be indicated in the appended claims.

BRIEF DESCRIPTION OF THE DRAWINGS

For a fuller understanding of the nature and objects of the present invention, reference is made to the following specification which is to be read in reference to the accompanying drawings, wherein.

DETAILED DESCRIPTION OF THE PREFERRED EMBODIMENT

Figure 1:
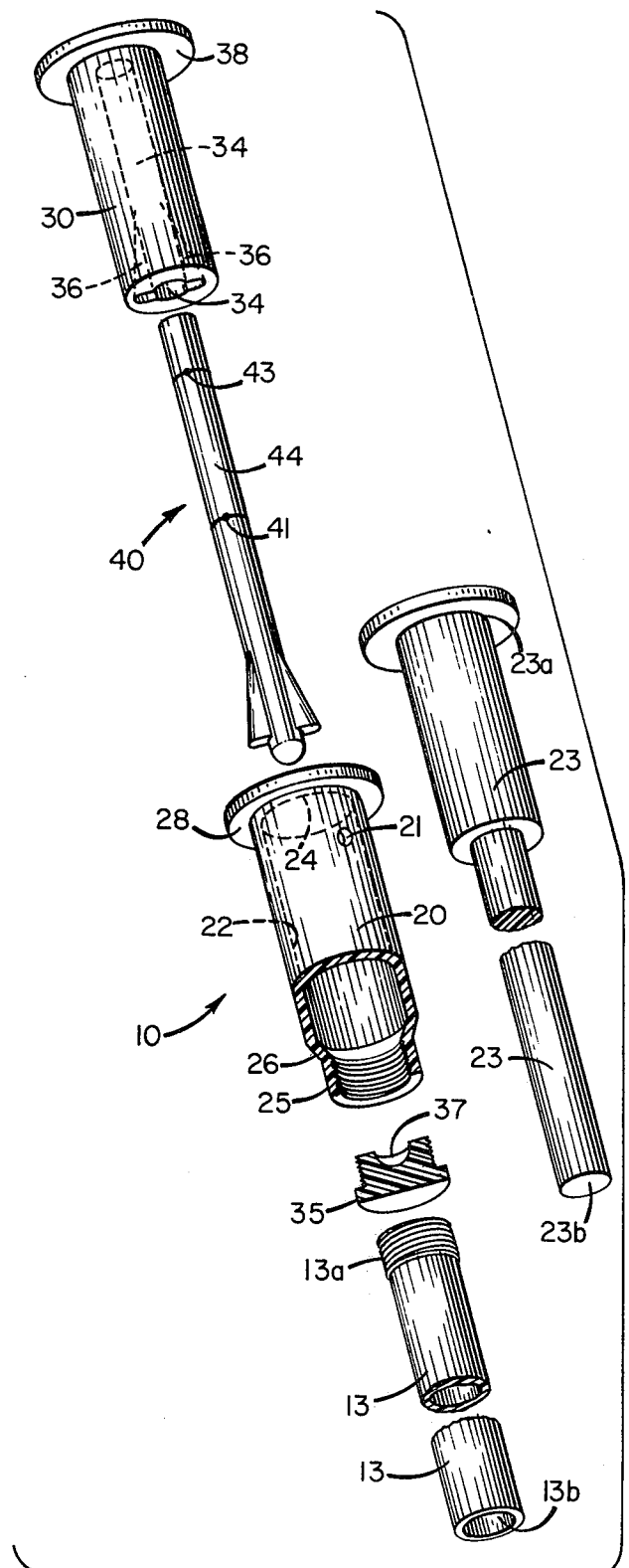
FIG. 1 is a perspective and exploded view of the various component parts of a disposable orthopedic implement constructed in accordance with and embodying the present invention and useful as a bone cement mixer and dispenser, employing but one and the same closed system for both mixing and dispensing in accordance with the present invention.

A preferred embodiment of the disposable orthopedic implement is shown in perspective and in an exploded view in FIG. 1. These elements when assembled, as more fully described below, permit bone cement to be mixed in and dispensed from one and the same closed system, thereby avoiding undue exposure to ambient contaminants. The reference character 10 denotes the disposable orthopedic implement and it is shown as comprising a cylindrical member 20 which may be a barrel whose hollow inside 22 defines a chamber utilized for both mixing therein and dispensing therefrom the bone cement. This barrel 20 is shown having an open upper end 24 and a lower narrowed end 26, and is also provided with an open neck 25 which may be internally threaded. This lower narrowed end 26 of barrel 20 terminating in the neck 25 may serve in combination, as the dispensing nozzle for the bone cement mixer and dispenser 10. In the alternative, if desired, an extension tube 13 having an externally threaded portion 13a and an open bottom end as at 13b may be conveniently secured within the externally threaded neck 25, thereby extending in effect the dispensing nozzle by the length of the extension tube 13. In some instances, a surgeon may desire to utilize such an extension tube wherein the application of the cement in a particular cavity of the human body so requires it.

During the mixing operation, the neck 25 is closed by a closure member 35 such as an externally threaded cap which may be conveniently secured within the internally threaded neck 25 so as to hermetically seal off the same. As may be noted, closure member 35 is formed with a central depression 37 whose significance will more fully appear hereinafter. The open upper end 24 of the barrel 20 is peripherally provided with a flange portion 28 by means of which a surgeon, if manually operating the disposable orthopedic implement, will dispense the mixed cement therefrom through its open neck 25, as more fully described below.

The member designed for reciprocation within the chamber 22 of the barrel 20 is preferably a plunger 30 whose diameter is designed so that the plunger fits snugly but slidably within the chamber 22 so that it may be axially displaced therein. As may be noted, the plunger at its upper end is also provided with a flange 38 which cooperates with the flange 28 of barrel 20 during the dispensing operation by allowing the surgeon to exert pressure on this flange 38 so as to axially displace the plunger 30 within the barrel 20. The bottom end of plunger 30 may be formed as shown, or if desired, it may be tapered so as to fit the lower narrowed end 26 of the barrel 20. When so tapered, plunger 30 may then better serve to evacuate the mixture of bone cement therefrom through the open neck 25. The plunger 30 is formed with an internal contoured opening 34 which, for the most part, is an axial channel that extends throughout the length thereof. Additionally there are formed tapered sections 36,36 communicating with the axial channel which sections 36,36 extend from about the center of the plunger 30 toward the bottom end thereof, substantially as shown. The function of this internal contoured opening 34 is to receive therein a mixing member 40 which essentially comprises a shaft consisting of a long top shaft section 44 and a short bottom shaft section 42. A pair of mixing paddles (vanes) 46,46 are provided adjacent the short bottom shaft section 42 and radially extending from the shaft. These mixing paddles (vanes) 46,46 of the mixing member 40 are responsible for effecting the mixing operation within the chamber 22 of the cylindrical member 20 when assembled, as will be more apparent hereafter. Mixing member 40 is provided with two markers about its long top shaft section 44. The first marker 41 is located about the center portion of the shaft while the second marker 43 is located near its upper end portion, substantially as shown. These markers 41 and 43 are utilized during assembly of the mixing member 40 and the plunger 30 just prior to the commencement of the loading of the barrel 20 with the cement components and during and after the mixing operation, as will be more apparent from below.

It is to be noted that the barrel 20 is also provided at its upper portion with a port 21 that is designed for attachment to a suitable vacuum source by means of a vacuum tube 19 so as to remove the effluent gas and any toxic fumes generated during the mixing operation of the cement components in chamber 22. It should also be noted that when a surgeon considers the need for using extension tube 13 as hereinabove mentioned, then plunger 30 will be displaced by the extension tube plunger 23 so as to dispense the mixed cement through the extension tube 13. The extension tube plunger has a shoulder region of increased diameter to engage the inner surface of the barrel in order to maintain its correct position within the barrel. Extension tube plunger 23 is essentially a cylindrical member having a solid bottom portion 23b and an upper flange 23a. It can otherwise be hollow. Again, the extension tube plunger 23 is designed with a diameter slightly less than the internal diameter of the extension tube 13 so as to snugly but slidably fit therein. Preferably, the surgeon will first utilize the plunger 30 to dispense the already mixed cement from inside the chamber 22 into the extension tube 13 prior to the removal of plunger 30 and the introduction of the extension tube plunger 23 therein. In this fashion, the cement mixture already finds itself for the most part within the extension tube 13. As may also be noted, the mixing member 40 together with its vanes or paddles 46,46 and the internal contoured opening 34 formed within the plunger 30 are so designed that the long top shaft section 44 may be axially disposable within the contoured opening and, as long as paddles 46,46 remain clear of the tapered sections 36,36, the mixing member 40 may conveniently be rotated within the plunger 30 by the application of torque to the upper end of the shaft thereof projecting through plunger 30 beyond its flange 38. This torque is preferably exerted by either a pneumatic or an electric drill whose jaws may be removably attached thereto, as will be more fully described with reference to FIG. 3.

These elements of the disposable orthopedic implement 10 shown in exploded perspective view and described with reference to FIG. 1, may conveniently be made, as by injection molding so as to form a rigid polymer, preferably a light transmitting rigid polymer, for example, an acrylic such as methyl methacrylate or an olefin such as polyethylene or polypropylene. Furthermore, it should be noted that these elements are designed for one use only and after use, they should be discarded. Also, all these elements are sterilizable and are sterilized prior to use.

Figure 2:
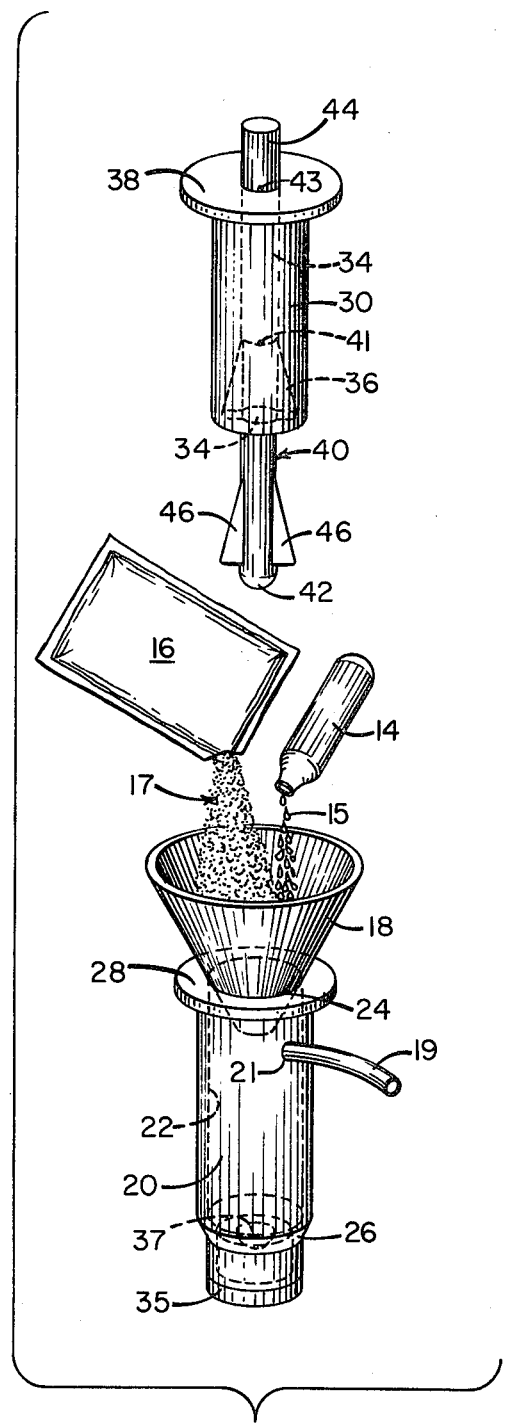
FIG. 2 is a perspective view of the elements of the disposable orthopedic implement shown in FIG. 1 in a condition showing the introduction for mixing of the powder and liquid components of the bone cement into a barrel by utilizing a funnel, and also showing the mixing member partially introduced within the plunger preparatory to the mixing operation.

FIG. 2 is a perspective view of the various above-described elements of the disposable orthopedic implement 10 assembled in two subassemblies in condition for the introduction of the power and liquid components of the bone cement into the barrel by the utilization of a convenient funnel 18. It must be noted that just immediately prior thereto, port 21 communicating with the hollow inside chamber 22 has been connected to a source of vacuum (not shown) by vacuum tube 19. This is to enable the removal from the chamber 22 of all of the effluent gas and toxic fumes that will be generated during the mixing of the two component parts of the bone cement therein. The first subassembly is of course effected by the application of the externally-threaded cap 35 representing the closure member to the internally-threaded open neck 25 of the barrel 20, hermetically sealing it off thereby. Bone cement is preferably prepared immediately prior to use as a mixture of a polymerizate, such as a liquid methyl methacrylate monomer and an activator such as a powdered mixture of polymethyl methacrylate, barium sulfate and benzoyl peroxide. The liquid cement portion is contained in an ampule 14 and may have ten (10) ml or twenty (20)ml therein, depending upon the use, i.e., whether it is for a knee, requiring a small dose, or for a hip requiring a larger dose. The powder is normally packaged in a plastic pouch 16, again containing either 20 grams or 40 grams, depending whether it is going to be used with a 10 ml ampule as a knee dose or with a 20 ml ampule as a hip dose. These powders and liquids and the ampules and pouches have been pre-sterilized when packaged in their respective containers. In the introduction of these bone cement component parts through the funnel 18, it is important to remember that first the powder contained in the pouch 16 must be introduced by emptying its contents through the funnel 18 into the hollow inside chamber 22 of the barrel before permitting the liquid cement component contained in ampule 14 to be introduced therein. This introduction sequence is significant since immediately upon the introduction of the liquid component, the polymerization process between the two bone cement components commences. Consequently, once the ampule 14 has also been emptied into the hollow inside chamber 22 of the barrel, funnel 18 should be immediately withdrawn and the second subassembly represented by the combination of the plunger 30 with the mixing member 40 inserted therein, is then immediately introduced partly into the chamber 22 of the barrel 20 through its upper open end. It should be noted that the mixing member 40 has been introduced into the contoured opening 34 of the plunger 30 so that its upper marker 43 is just barely visible above the flange 38 thereof. This is significant since this allows the paddles or vanes 46,46 to remain clear of the tapered sections 36,36 also formed in the plunger 30, as previously mentioned. The plunger 30 together with its mixing paddle member 40 is introduced within the hollow inside chamber 22 of the barrel 20 until such time that its short bottom shaft section 42 comes to seat within the central depression 37 concentrically formed in the cap 35, as may be best observed in FIG. 3. In this fashion it is assured that paddles 46,46 come in contact with the introduced cement components 27 contained in the bottom part of the chamber 22, and also that the paddles 46,46 have a slight clearance for rotation above the cap 35.

Figure 3:
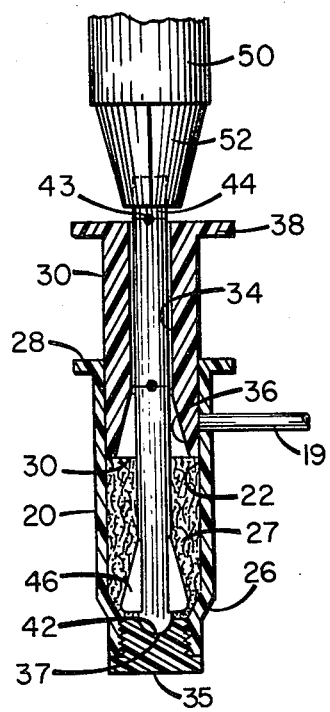
FIG. 3 is a cross-sectional view of the disposable orthopedic implement of the invention in an assembled condition, with the mixing member and the plunger partly introduced within the cylindrical member, preparatory to mixing the cement components already introduced in the chamber and fragmentarily showing a pneumatic or electric drill operatively connected to the mixing member.

As may be noted in FIG. 3, the mixing paddle member 40 is now ready to be connected at the upper end of its long top shaft section 44 to the gripping jaws 52 of either a pneumatic or electric drill 50 for effecting the mixing operation. This may be accomplished by holding the disposable orthopedic implement 10 in this assembled condition in a stand for mixing by the pneumatic or electric drill 50 and keeping it there for the required amount of time, normally about 3 to 4 minutes. Under these circumstances, for example, the stand is provided with a suitable support, by which implement 10 is snapped into place and a motor operating through gripping jaws 52 drives the upper end of the shaft 44 of the mixing member 40.

Figure 4:
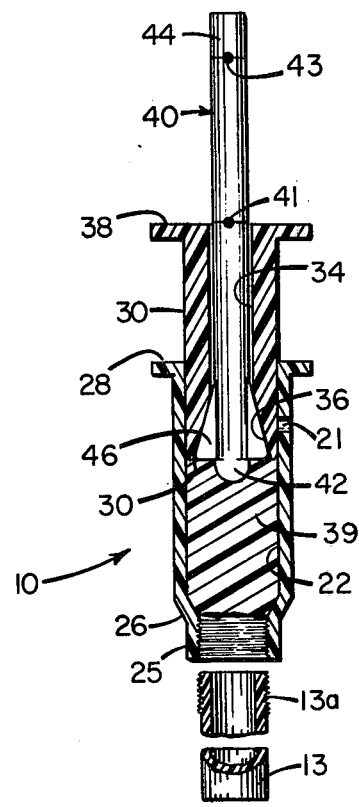
FIG. 4 is a view similar to that shown in FIG. 3, but showing the position after the mixing operation of the cement components has been completed and with the mixing member completely withdrawn into the plunger and the drill disconnected from the mixing member, and also after the removal of the closure member and just prior to the implement being used by a surgeon for the dispensing of the already mixed cement from this closed system into a patient; herein the dispensing may be by hand.

During the mixing operation, the powder and liquid components 27 of the bone cement within the chamber 22 of the barrel 20 will be transformed to a thoroughly mixed and kneaded bone cement 39 that is soft and pliable and thus ready for dispensing to fill the bone cavity and mechanically to fix the prosthesis. As shown in FIG. 4, first the gripping jaws 52 of the penumatic or electric drill 50 are disengaged from the upper end of the top shaft section 44 and then the mixing paddle member 40 is now completely introduced into the internal contoured opening 34 of the plunger 30 by simply gripping the shaft 44 and pulling at it until the marker 41 appears above flange 38. Of course, the mixing paddles 46,46 first will have to be aligned with the tapered sections 36,36, which can easily be accomplished by slightly rotating shaft 44 while also exerting a pulling force thereon. This complete introduction of the entire mixing member 40, in particular its mixing paddles or vanes 46,46 within the tapered sections 36,36 of the plunger 30 is important for two reasons. First, it permits the removal of any excess mixture of cement from the paddles 46,46 and, second it permits the quick and easy dispensing of the mixed cement 39 therefrom by already having accommodated the paddles 46,46, in the tapered sections 36,36. The resulting flush bottom surface of the plunger 30 now exerts a uniform extrusion force on the mixed bone cement 39. The surgeon is of course assured as to when the mixing paddle member 40 has been completely withdrawn within the contoured internal opening 34 of the plunger by observing the appearance of the second marker 41 on shaft 44 above the flange 38.

Following the disengagement of the shaft 44 and its withdrawal into the internal contoured opening 34 of the plunger 30, the vacuum source is also disconnected by removing the vacuum tube 19 from port 21. As may be noted from the figures, particularly FIG. 4, port 21 is formed near the upper open end 24 of the barrel 20 so as to find itself in the area well above the mixed bone cement 39, an area which is occupied by the plunger 30 during and immediately after the mixing operation, as may be best noted in FIGS. 3 and 4. Consequently, no mixed cement 39 may escape through this port 21 during the dispensing operation.

Figure 5:
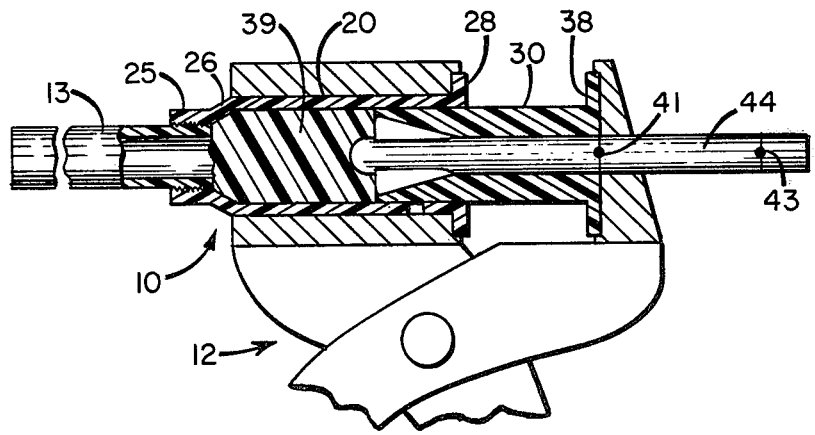
FIG. 5 shows the same dispensing system as in FIG. 4 with the already mixed cement therein but with the disposable orthopedic implement mounted within a suitable evacuation implement, such as a caulking gun.

The operator, who may well be the surgeon, will then remove the closure member 35 by unscrewing the same from the neck 25 and now the implement 10 is ready for applying the bone cement into a bone cavity of a patient. This dispensing operation may take place immediately by the surgeon's simply grasping the disposable orthopedic implement 10 in the palm of his hand and with his thumb applying pressure on the flange 38 of the plunger. While holding the other flange 28 of the cylindrical member 20 firmly in his hand, he slowly and steadily displaces axially the plunger 30 within the hollow inside chamber 22 toward its lower narrowed end 26, so as to dispense gradually the mixed bone cement 39 through the now open neck 25 into the bone situs. The surgeon, if he wishes, may utilize a mechanical force for the dispensing operation, as shown in FIG. 5. If so, the disposable orthopedic element 10 is first positioned within such a mechanical device, which may be a caulking gun as shown, so as to position the flange 28 of the barrel 20 in its front jaw and the flange 38 of the plunger 30 in its rear jaw. Then as is well known, by taking the caulking gun in hand, he may easily effect the axial displacement of the plunger 30 within the cylindrical member 20 by pistol-gripping and moving the two arms of the caulking gun together.

Since certain changes may be made in the present disclosure, it is intended that all matter described in the foregoing specification or shown in the accompanying drawings be interpreted in an illustrative and not in the limiting sense.

What is claimed is:

1. A disposable orthopedic implement formed of a rigid polymer and designed to mix bone cement in and dispense from a closed system comprising:
   (a) a chamber having a barrel portion and a neck portion;
   (b) a member reciprocable within said barrel portion of said chamber;
   (c) a mixing member operatively and axially receivable within said reciprocable member; and
   (d) means for rotating said mixing member within said barrel portion of said chamber.

2. The disposable orthopedic implement of claim 1 wherein said mixing member comprises a member having a pair of paddles.

3. A disposable orthopedic implement designed to mix bone cement in and dispense from a closed system comprising:
   (a) a barrel defining a chamber and having a neck;
   (b) a plunger reciprocable within said barrel and having an internal contoured opening;
   (c) a paddle member having a short bottom shaft section and a long top shaft section and designed to be axially disposed within said internal contoured opening;
   (d) a closure member fitting about said neck; and
   (e) means to rotate said paddle member when said top shaft section is disposed within said plunger which in turn is disposed within said barrel so that said short bottom shaft section extends into said neck.

4. The disposable orthopedic implement of claim 3 in which said barrel, said plunger, said paddle member and said closure member are made of a rigid polymer.

5. The disposable orthopedic implement of claim 3 in which said neck is internally threaded and said closure member is externally threaded for cooperative meshing.

6. A disposable orthopedic implement having mixer and dispenser elements designed to mix bone cement in and dispense from a closed system comprising:
   (a) a barrel defining a chamber and having an open upper end provided with a flange, a lower narrowed end with an internally threaded neck, and a port for connection to a vacuum source;
   (b) a plunger reciprocable within said barrel and having a flange and an internal contoured opening;
   (c) a mixing member having a pair of paddles disposed radially about a shaft having a short bottom shaft section and a long top shaft section, said mixing member designed to be axially disposed within said internal contoured opening of said plunger;
   (d) an externally threaded closure member cooperatively fitting about said internally threaded neck of said barrel for closing same and provided with a central depression; and
   (e) means to rotate said mixing member when its said long top shaft section is disposed within said plunger which in turn is disposed within said barrel so that said short bottom shaft section extends into said neck.

7. The disposable orthopedic implement of claim 6, in which said barrel, said plunger, said mixing member and said closure member are made of a rigid polymer.

8. A method for mixing bone cement in and for dispensing from a closed system comprising the steps of:
   (a) providing a cylindrical member having a chamber and a plunger for reciprocation within said member;
   (b) providing a mixing member designed for axial displacement within said plunger;
   (c) partially inserting said mixing member into said plunger;
   (d) introducing measured amounts of a powdered cement component and of a liquid cement component into said chamber;
   (e) inserting said plunger together with said mixing member partly into said chamber so that said mixing member communicates with said introduced amounts of cement components therein;
   (f) rotating said mixing member so as to mix said cement components within said chamber;
   (g) completely inserting said mixing member into said plunger; and
   (h) dispensing said mixture from said chamber by axially displacing said plunger within said cylindrical member.

9. A method for mixing bone cement in and for dispensing from a closed system comprising the steps of:
   (a) providing a cylindrical member having a chamber and a port, and a plunger for reciprocation within said member;
   (b) providing a mixing member designed for axial displacement within said plunger;
   (c) partially inserting said mixing member into said plunger;
   (d) introducing measured amounts of a powdered cement component and of a liquid cement component into said chamber;
   (e) connecting a source of vacuum to said port communicating with said chamber;
   (f) inserting said plunger together with said mixing member partly into said chamber so that it communicates with said introduced amounts of components;
   (g) rotating said mixing member so as to mix said cement components within said chamber;
   (h) completely inserting said mixing member into said plunger;
   (i) disconnecting said source of vacuum from said port; and
   (j) dispensing said mixture from said chamber by axially displacing said plunger within said cylindrical member.

10. A method for mixing bone cement in and for dispensing from a closed system comprising the steps of
   (a) providing a barrel having a chamber, a neck and a port;
   (b) closing said neck;
   (c) providing a plunger for reciprocation within said barrel and having an internal controured opening;
   (d) providing a member having a pair of mixing paddles and designed for axial displacement within said contoured opening;
   (e) inserting said member into said contoured opening so that its said pair of mixing paddles remain clear of said opening;
   (f) introducing measured amounts of a powdered cement component and of a liquid cement component into said chamber;
   (g) connecting a source of vacuum to said port communicating with said chamber;
   (h) inserting said plunger carrying said member partly into said chamber so that said pair of mixing paddles enter into said introduced amounts of cement components therein;

(i) rotating said member having said pair of mixing paddles for a predetermined time, thereby thoroughly mixing said cement components within said chamber;

(j) inserting further said member into said contoured opening until its said pair of mixing paddles are entirely accomodated therein;

(k) opening said neck and disconnecting said source of vacuum from said port; and (l) dispensing said mixture from said chamber through said neck by axially displacing said plunger within said barrel toward said neck.

* * * * *